United States Patent [19]
Weissman

[11] Patent Number: 4,571,187
[45] Date of Patent: Feb. 18, 1986

[54] DENTAL POST FOR RETENTION OF A PROSTHETIC SUPERSTRUCTURE

[75] Inventor: Bernard Weissman, New York, N.Y.

[73] Assignee: Ipco Corporation, White Plains, N.Y.

[21] Appl. No.: 661,722

[22] Filed: Oct. 17, 1984

Related U.S. Application Data

[63] Continuation-in-part of Ser. No. 489,942, Apr. 29, 1983, Pat. No. 4,479,783.

[51] Int. Cl.⁴ ............................................. A61C 5/08
[52] U.S. Cl. ................................................. 433/221
[58] Field of Search ............... 433/220, 221, 222, 174, 433/175, 176, 203

[56] References Cited

U.S. PATENT DOCUMENTS

| | | | |
|---|---|---|---|
| 2,536,669 | 1/1951 | Thau-Jensen | 433/221 |
| 3,521,357 | 7/1970 | Berglund et al. | 433/26 |
| 4,177,562 | 12/1979 | Miller et al. | 433/174 |
| 4,268,253 | 5/1981 | Gross et al. | 433/221 |

FOREIGN PATENT DOCUMENTS 2225863  4/1980  Fed. Rep. of Germany ...... 433/225

Primary Examiner—Robert Peshock
Attorney, Agent, or Firm—Goodman & Teitelbaum

[57] ABSTRACT

A dental post for retaining a dental restoration in a secured position on a prepared tooth stub, the dental post including a cylindrical elongated pin having grooves disposed about the periphery thereof, the pin being insertable within a bore provided in the tooth stub. A head portion of the pin projects from the tooth stub to secure the restoration thereon. The head portion includes a substantially conical neck section from which projects a flattened tang. The tang is substantially wider than the diameter of the pin and is angularly oriented with respect to the elongated axis of the pin. The head portion provides improved retention of the superstructure upon the tooth stub and permits orientation of the tang in the same angled direction as the angular orientation of the tooth prosthesis so as to be centrally located within the tooth superstructure for improved retention and strength.

23 Claims, 8 Drawing Figures

DENTAL POST FOR RETENTION OF A PROSTHETIC SUPERSTRUCTURE

RELATIONSHIP OF OTHER APPLICATIONS

This invention is a continuation-in-part application to co-pending U.S. Application Ser. No. 489,942 filed on Apr. 29, 1983 now U.S. Pat. No. 4,479,783 issued 10/30/84 by the Applicant of the present invention for an invention entitled "Helically Fluted Dental Post".

BACKGROUND OF THE INVENTION

This invention relates to a dental post which can be securely inserted into a tooth stub. The dental post has an angularly oriented head portion which extends from the tooth stub for improved retention of a dental restoration built onto the tooth stub.

In restoring dentition, it is well known in the field of dentistry to build up a dental prosthetic structure onto a tooth stub for replacement of missing dentition. The tooth stub is initially prepared by cutting it down to provide a suitable support on which the prosthetic structure will be placed. A bore is formed into the tooth stub in which a dental post is inserted. The dental post generally includes grooves formed thereabout for improving the retention of the post in the bore formed in the tooth stub. Suitable dental cement is used for such retention. A portion of the dental post extends upwardly above the surface of the tooth stub so that as the dental prosthetic structure is formed or built up onto the tooth stub, it is retained in place on the tooth stub by means of the extending portion of the dental post.

Numerous types of dental posts have been suggested in the prior art. Some of these include a thread peripherally formed about a cylindrical pin into which the dental cement can penetrate in order to provide additional retention of the dental post in the bore. In the aforementioned parent application, there is described a dental post which includes helical flutes formed into the external surface of the cylindrical pin. The flutes have a pitch which is greater than the length of the pin. Some of the flutes can have greater width and depth size than other flutes. In some dental pins, there is also provided a vent to permit the escape of the air within the bore during insertion of the post into the cement prepared bore of the tooth stub.

The aforementioned dental posts provide improvements with respect to the retention of the post in the bore. However, the extending head portion of the post is also utilized for the retention of the prosthetic structure onto the tooth stub. Accordingly, appropriate attention must be given to the head portion to be sure that it provides sufficient retention of the superstructure onto the tooth stub.

SUMMARY OF THE INVENTION

Accordingly, it is an object of the present invention to provide an improved dental post.

A further object of the present invention is to provide an improved dental post having a head portion for increased retention capability of a prosthetic superstructure built or formed onto a tooth stub.

Still a further object of the present invention is to provide a dental post having a head portion which extends outwardly from the tooth stub which the restoration can be secured, and which provides improved retention of the restoration onto the tooth stub.

Yet another object of the present invention is to provide a dental post having a head portion which projects therefrom, which head portion will be embedded into the dental restoration built onto the tooth stub such that the head portion remains centrally located within the dental restoration.

Another object of the present invention is to provide a dental post having a head portion extending from the cylindrical pin, and including a flattened tang angularly oriented with respect to the cylindrical pin.

Briefly, in accordance with the present invention, there is provided a dental post for retaining a dental restoration secured onto a prepared tooth stub. The dental post includes an elongated cylindrical pin with preferably helical grooves disposed about the periphery of the pin for retaining the pin secured within a cement prepared bore in the tooth stub. A head portion extends from the pin. Upon insertion of the pin in the bore, the head portion projects outwardly from the tooth stub. It is upon the head portion that the restoration can be secured. The head portion includes a flattened tang which provides improved retention of the dental restoration onto the tooth stub.

In an embodiment of the present invention, the tang is angularly oriented or inclined with respect to the elongated axis of the pin. The tang can have a width greater than the diameter of the pin, and can be formed with its lateral sides upwardly tapered so that the width at the bottom of the tang is greater than the width at the top thereof. Projecting ribs can be peripherally provides about the outer surfaces of the flattened tang for improving its retention capabilities. A suitable indicia can be formed on the tang for identification of the dental post as to its size, shape, or the like. The indicia can project from the surface of the tang, and thereby also provide greater retention capabilities to the head portion.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings, of a preferred embodiment in which.

In the various figures of the drawing, like references characters designate like parts.

DETAILED DESCRIPTION OF THE PREFERRED EMBODIMENT

Figure 1:
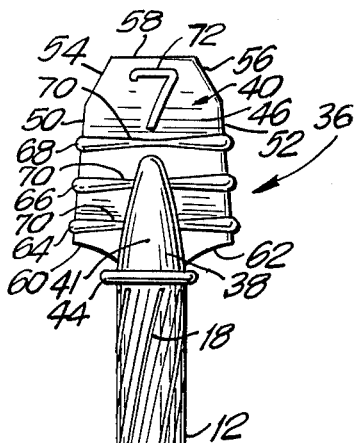
FIG. 1 is a front elevational view of a dental post in accordance with the present invention.

Referring now to FIG. 1, the dental post of the present invention is shown generally at 10. The post 10 includes an elongated cylindrical pin 12 having a lower chamfered end 14. Formed about the periphery of the pin 12 are a plurality of helical flutes 16. The helical flutes 16 are described in more detail in the aforementioned co-pending parent application. Briefly, however, the flutes 16 have a very large pitch, with the pitch of each flute being greater than the length of the pin 12. Because of the large pitch of the flutes 16, a large number of separate individual helices can be provided, where the flutes 16 are spaced apart. In this manner, there are a plurality of separate longitudinally disposed flute lines that begin and terminate along the length of the pin 12. Preferably, the pitch is approximately one revolution per inch, and the pin length is approximately 0.750 inches.

Because the multiple flute lines terminate the bottom of the pin, where the spiral path of each of the flutes is less than one revolution about the pin, there are a plurality of paths that are available for escape of the air from the bore as the pin is inserted into the bore formed in the tooth stub. The hydrostatic pressure can therefore be reduced as the air escapes along the multi-flute lines, each of which provides a separate venting path. Accordingly, no separate vent path need be provided in the pin. Preferably, the pitch of each of the flutes 16 provides a pitch angle of less than 10 degrees with respect to the longitudinal axis of the pin 12 to maintain the venting capability of the flutes 16.

Thus, the flute lines provide two purposes. Firstly, they provide an improved retention benefit within the bore, and accordingly when the pin 12 is inserted into the bore, the cement will retain the pin 12 securely positioned within the tooth stub. Secondly, they simultaneously serve as venting channels for the pin 12.

Figure 5:
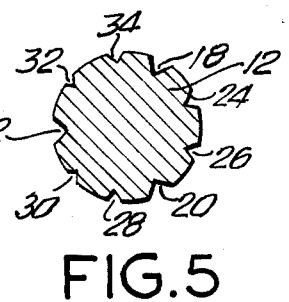
FIG. 5 is a cross sectional view taken along line 5—5 of FIG. 1, showing one type of helical grooves that can be provided about the pin portion.

As shown in FIG. 5, the grooves of the flutes 16 can be formed of different sizes, where the depth of the flutes is smaller than the spacing between adjacent flutes. As particularly shown, there is a set of three grooves 18, 20, 22, all of a larger size, and there are sets of grooves of a smaller size therebetween. Specifically, a pair of smaller grooves 24, 26 are formed between the larger grooves 18 and 20. Similarly, a pair of smaller grooves 28, 30 are formed between the larger grooves 20 and 22, and an additional pair of smaller grooves 32, 34 are formed between the grooves 18 and 22. Accordingly, the flutes 16 are cut into the pin 16 to a respective depth defining at least one minor diameter so that at any cross section taken along the longitudinal axis of the pin there exists a greater peripheral length at the major diameter of the pin than at the minor diameter.

Although a series of larger and smaller flutes have been shown, it should be appreciated that the pin can be provided with just the larger size flutes or the smaller size flutes, or other combinations thereof, or merely with threads or grooves therein.

Thus, it should also be appreciated that although the particular pin is shown as having helical flutes, the present invention could be provided with an elongated post having a standard external spiral thread formed thereabout. In addition, the pin could include an elongated vertical channel provided through the external threads to serve as a vent during insertion of the post into the tooth stub.

Referring now to FIGS. 1–4, it will be noted that projecting from one end of the pin 12 there is provided a head portion, shown generally at 36. The head portion 36 includes a substantially conical neck section 38 which supports a flattened tang 40. The conical section 38 includes a pair of opposing front and rear portions 41, 42 which are separated by the tang 40 serving to bifurcate the conical section 38. An annular collar 44 peripherally projects at the interface between the pin 12 and the head portion 36.

The flattened tang 40 includes substantially flat front and rear surfaces 46, 48 with thin side walls 50, 52. The tang is tapered in an upwardly direction so that the width of the tang at its upper end is less than at its lower end. Additionally, the upper end has a further angularly tapered tip section 54, 56 terminating in a flat top wall 58. The bottom of the tang 40 includes arcuately shaped shoulders 60, 62 which merge into the conical section 38.

A plurality of projecting ribs are formed peripherally about the tang 40. Specifically, three longitudinally spaced apart ribs 64, 66, 68 are shown. The ribs have their mid sections 70, which occur along the flattened front and rear surfaces 46, 48, slightly thinner than the rib thickness at the lateral ends thereof.

Figure 3:
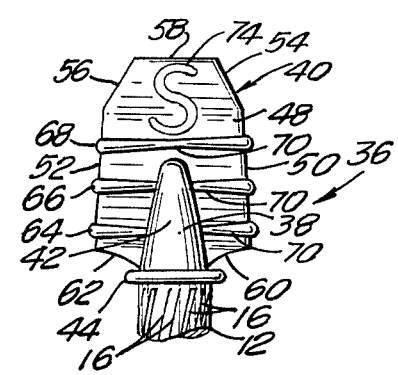
FIG. 3 is a front elevational view of the head portion.

An indicia, such as 72 in FIG. 1 or 74 in FIG. 3, can be formed on the upper end of the front or rear face of flattened tang 40 in order to provide identification of the size of the dental post, or provide its particular quality or use. This indicia can project from the surface of the tang 40.

Figure 2:
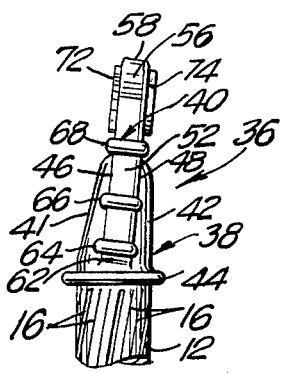
FIG. 2 is a side elevational view of the upper end of the dental post shown in FIG. 1, specifically showing the angular orientation of the head portion.
Figure 4:
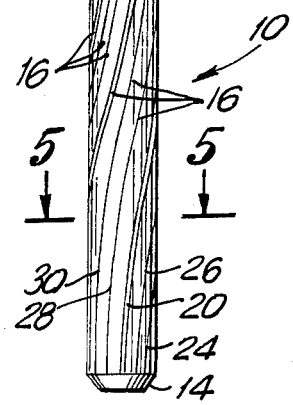
FIG. 4 is a top view of the dental post shown in FIG. 1.

As best shown in FIGS. 2 and 4, the tang 40 is angularly oriented with respect to the elongated axis of the post, preferably 7 to 8 degrees. Additionally, as can be noted in FIG. 2, the conical neck section 38 is also offset such that its front portion 41 is angled with respect to its rear portion 42, so as to be similar to the 7 to 8 degrees of inclination of the tang 40 in order to accommodate the angular orientation of the tang projecting therefrom. The width of the tang 40 is greater than the diameter of the pin 12, where the thickness of the tang 40 is less than the diameter of the pin 12, as best shown in FIG. 1–4.

The particular structure of the head portion 36 provides improved retention of the superstructure onto the tooth stub. Specifically, the width of the tang 40 is large such that it can provide retention of the superstructure. Furthermore, having the tang tapered so that its bottom portion is wider than the top portion, again provides additional retention of the superstructure and conforms to the shape thereof. Likewise, the shaped ribs and the projecting indicia aid in such retention, as does the presence and shape of the conical neck section 38, where the annular collar 44 indicates the proper depth of insertion of the pin 12 into the tooth bore and can function as a stop, as set forth below.

Of significance is the fact that the tang 40 is angularly oriented with respect to the elongated axis of the pin. This again aids in retaining the superstructure upon the tooth stub. Furthermore, and especially in connection with anterior teeth, the angled orientation of the tang 40 serves to position the tang centrally within such anterior teeth where the tang has an angled orientation similar to the anterior teeth. As is well known, anterior teeth are angularly shaped. Therefore, the tooth prosthesis replacing such angled teeth will also be angularly shaped. Accordingly, by inserting the dental post into the tooth stub, such that the angular orientation of the tang 40 corresponds to the angular direction of the tooth prosthesis, the tang can be located so as to be centrally positioned within the tooth superstructure so that the thickness of the superstructure is uniform about the tang. This provides not only greater retention, but also improved strength to the superstructure. Furthermore, the shadow effect of the dental post, as shown in the dental art, is eliminated due to the shape of the tang 40.

Figure 6:
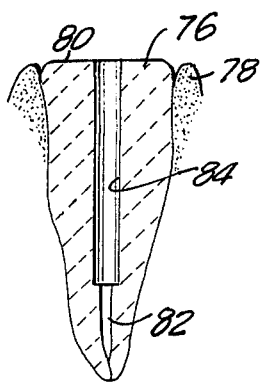
FIG. 6 is a cross sectional view taken through a tooth stub showing the preparation of the tooth stub for utilization of the dental post of the present invention.
Figure 7:
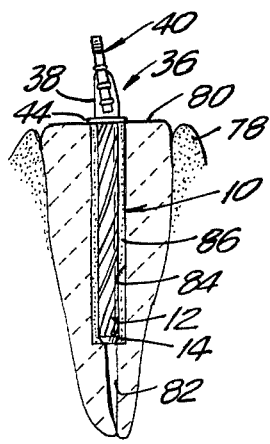
FIG. 7 is a cross sectional view similar to that shown in FIG. 6, showing the inserted dental post of the present invention.
Figure 8:
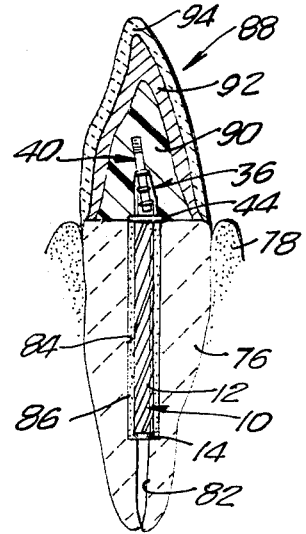
FIG. 8 is a cross sectional view similar to that shown in FIG. 7, showing the dental restoration placed upon the tooth stub.

Referring now to FIGS. 6–8, the method utilized for the present dental posts 10 will be briefly described. By way of example, there is shown in FIG. 6, a tooth stub 76 within the gum area 78, where the upper end of the tooth (not shown) has been previously broken. To prepare the tooth, the tooth has been initially cut down as known in the dental art, typically to provide a suitable upper surface 80. In order to build up a superstructure onto the tooth stub 76, there is required a retaining member, such as a dental post.

Initially, conventional root canal work is carried out by drilling and cleaning out of the pulp along the canal section 82 of the tooth stub. Subsequently, an enlarged bore 84 is drilled into the tooth stub 76 of a size larger than the diameter of the pin 12, but commensurate with the periphery of the annular collar 44 of the dental post to be inserted. Cement 86 is then placed into the bore 84 and onto the dental post 10 of the present invention. The pin 12 of the post 10 is then inserted into the bore 84. The cement 86 fills the flutes or helical grooves or threads defined about the periphery of the pin and also aurrounds the pin itself. The pin 12 is inserted into the bore 84 until the collar 44 sits at the mouth of the bore and serves as a stop for further insertion, whereby the proper depth of insertion of the pin 12 has been reached, as shown in FIG. 7.

The head portion 36 of the post extends upwardly above the surface 80 of the tooth stub. A superstructure 88 can then be suitably formed onto the tooth stub in accordance with standard well known techniques in the dental art.

Initially, a composite or plastic material build-up 90 is formed on the extending head portion 36 of the dental post. Such composite or plastic material build-up 90 can generally be done by the dentist himself. Appropriate impressions are then made and sent to a laboratory for the formation of the crown casting 92, typically formed of suitable metal material. Finally, at the laboratory, the upper porcelain or plastic outer crown 94 is formed on the casting 92, where the dentist fits the crown 92, 92 on the build-up 90 in a conventional manner, to complete the superstructure, as shown in FIG. 8.

The superstructure 88 is retained in place by means of the head portion 36, especially by means of the tang 40, as well as the conical neck section 38. It will be noted, in FIG. 8, that the dental superstructure 88 is typically shown as an anterior tooth. In such teeth, the angular orientation of the tooth is inward into the mouth, being toward the left as viewed in FIG. 8. Accordingly, the dental post is inserted so that the angular orientation of the tang 40 likewise is directed in the same direction as the tooth so as to be commensurate with the angular orientation of the tooth. In this manner, after the superstructure 88 is completed, the tang is substantially centrally located within the prosthesis. This provides improved retention as well as improved strength to the prosthesis.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental post for retaining a dental restoration in secured position on a prepared tooth stub, said dental post comprising:
   an elongated cylindrical pin having a predetermined diameter and a longitudinally extending axis;
   grooves disposed about a periphery of said pin for retaining said pin secured within a cement prepared bore in the tooth stub;
   a head portion extending from said pin for projecting outwardly from the tooth stub upon which the dental restoration can be secured when said pin is inserted into the tooth stub bore;
   said head portion including a flattened tang member for improved retention of the dental restoration upon the tooth stub;
   said tang member having a width greater than said pin diameter;
   said head portion including an upwardly tapering substantially conical neck section; and
   said tang member bifurcating said conical neck section for support thereby.

2. A dental post as in claim 1, wherein said tang member is angularly oriented with respect to said pin axis.

3. A dental post as in claim 1, wherein said width of said tang member is greater than a base width of said conical neck section.

4. A dental post as in claim 3, wherein said base width of said conical neck section proximates said diameter of said pin.

5. A dental post as in claim 1, including an annular collar projecting from an interface between said pin and said conical neck section.

6. A dental post as in claim 1, including a plurality of longitudinally spaced apart projecting ribs peripherally provided about said tang member for improved retention of the dental restoration upon the tooth stub.

7. A dental post as in claim 1, wherein said tang member is angularly oriented with respect to said axis of said pin, and a side of said conical neck section is angularly offset in a same orientation as said tang member.

8. A dental post as in claim 1, including indicia means provided on a flat surface of said tang member for identification of the dental post.

9. A dental post as in claim 1, wherein said pin includes flute means to define said grooves, said flute means including a plurality of external, spaced apart helical flutes providing separate spiral paths about said pin.

10. A dental post as in claim 9, wherein said flutes have a pitch greater than predetermined length of said pin so that each of said spiral paths is less than one revolution about said pin to define vents therein.

11. A dental post as in claim 9, wherein said tang member is angularly oriented with respect to said pin axis.

12. A dental post as in claim 1, wherein opposing sides of said tang member are inwardly tapered in a direction away from said pin such that a bottom portion of said tang member adjacent to said pin is wider than a top portion of said tang member spaced from said pin.

13. A dental post for retaining a dental restoration in secured position on a prepared tooth stub, said dental post comprising:

an elongated cylindrical pin having a predetermined diameter and a longitudinally extending axis;

grooves disposed about a periphery of said pin for retaining said pin secured within a cement prepared bore in the tooth stub;

a head portion extending from said pin for projecting outwardly from the tooth stub upon which the dental restoration can be secured when said pin is inserted into the tooth stub bore;

said head portion including a flattened tang member for improved retention of the dental restoration upon the tooth stub;

said tang member having a width greater than said pin diameter;

a plurality of longitudinally spaced apart projecting ribs peripherally provided about said tang member for improved retention of the dental restoration upon the tooth stub; and said projecting ribs including a thinner mid-section provided at opposing flat faces of said tang member than at lateral ends of said tang member.

14. A dental post as in claim 13, wherein said tang member is angularly oriented with respect to said pin axis.

15. A dental post as in claim 13, wherein opposing sides of said tang member are inwardly tapered in a direction away from said pin such that a bottom portion of said tang member adjacent to said pin is wider than a top portion of said tang member spaced from said pin.

16. A dental post as in claim 13, including indicia means provided on a flat surface of said tang member for identification of the dental post.

17. A dental post as in claim 13, wherein said pin includes flute means to define said grooves, said flute means including a plurality of external, spaced apart helical flutes providing separate spiral paths about said pin.

18. A dental post as in claim 17, wherein said flutes have a pitch greater than predetermined length of said pin so that each of said spiral paths is less than one revolution about said pin to define vents therein.

19. A dental post for retaining a dental restoration in secured position on a prepared tooth stub, said dental post comprising:

an elongated cylindrical pin having a predetermined diameter and a longitudinally extending axis;

grooves disposed about a periphery of said pin for retaining said pin secured within a cement prepared bore in the tooth stub;

a head portion extending from said pin for projecting outwardly from the tooth stub upon which the dental restoration can be secured when said pin is inserted into the tooth stub bore;

said head portion including a flattened tang member for improved retention of the dental restoration upon the tooth stub;

said tang member having a width greater than said pin diameter;

indicia means provided on a flat surface of said tang member for identification of the dental post; and said indicia means projecting from said flat surface of said tang member to improve the retention capabilities of said tang member.

20. A dental post as in claim 19, wherein opposing sides of said tang member are inwardly tapered in a direction away from said pin such that a bottom portion of said tang member adjacent to said pin is wider than a top portion of said tang member spaced from said pin.

21. A dental post as in claim 19, including a plurality of longitudinally spaced apart projecting ribs peripherally provided about said tang member for improved retention of the dental restoration upon the tooth stub.

22. A dental post as in claim 19, wherein said pin includes flute means to define said grooves, said flute means including a plurality of external, spaced apart helical flutes providing separate spiral paths about said pin.

23. A dental post as in claim 22, wherein said flutes have a pitch greater than predetermined length of said pin so that each of said spiral paths is less than one revolution about said pin to define vents therein.

* * * * *

Disclaimer and Dedication

4,571,187.—*Bernard Weissman,* New York, N.Y. DENTAL POST FOR RE-
TENTION OF A PROSTHETIC SUPERSTRUCTURE. Patent dated
Feb. 18, 1986. Disclaimer and Dedication filed June 4, 1986, by the as-
signee, *IPCO Corp.*

Hereby disclaims and dedicates to the Public claims 8, 16 and 19 through
23 of said patent.

[*Official Gazette August 5, 1986.*]